(12) United States Patent
Ding

(10) Patent No.: US 8,861,683 B2
(45) Date of Patent: Oct. 14, 2014

(54) MONOLITHIC CAPILLARY PARALLEL X-RAY LENS

(75) Inventor: Wei jiang Ding, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 365 days.

(21) Appl. No.: 13/338,477

(22) Filed: Dec. 28, 2011

(65) Prior Publication Data

US 2012/0163552 A1 Jun. 28, 2012

(30) Foreign Application Priority Data

Dec. 28, 2010 (CN) .......................... 2010 1 0622822

(51) Int. Cl.
*G21K 1/02* (2006.01)
*G02B 6/32* (2006.01)
*G21K 1/06* (2006.01)
*A61B 6/06* (2006.01)

(52) U.S. Cl.
CPC .. *G21K 1/067* (2013.01); *A61B 6/06* (2013.01)
USPC ............................. 378/145; 378/149; 359/809

(58) Field of Classification Search
CPC .............. G02B 3/00; G02B 3/02; G02B 6/32; G21K 1/02
USPC .......... 378/145, 147, 149, 204, 210; 359/362, 359/363, 618–620, 642, 708, 709, 809, 359/896; 385/33, 68
See application file for complete search history.

(56) References Cited

U.S. PATENT DOCUMENTS

| | | | |
|---|---|---|---|
| 4,167,675 A | 9/1979 | Stodberg et al. | |
| 4,910,759 A | 3/1990 | Sharnoff | |
| 5,175,755 A * | 12/1992 | Kumakhov | 378/34 |
| 5,812,631 A * | 9/1998 | Yan et al. | 378/85 |
| 6,583,420 B1* | 6/2003 | Nelson et al. | 250/397 |
| 6,754,303 B2 | 6/2004 | Kasumi | |
| 7,231,015 B2 | 6/2007 | Kumakhov | |
| 7,508,907 B2 | 3/2009 | Sasayama | |
| 2002/0148808 A1* | 10/2002 | Bjeoumikhov | 216/9 |
| 2003/0133536 A1 | 7/2003 | Kuwabara et al. | |
| 2003/0209677 A1* | 11/2003 | Kumakhov | 250/505.1 |
| 2006/0133575 A1* | 6/2006 | Gutman et al. | 378/119 |
| 2009/0046831 A1 | 2/2009 | Wong et al. | |
| 2009/0279670 A1* | 11/2009 | Verman et al. | 378/145 |
| 2011/0243305 A1* | 10/2011 | Tada | 378/87 |

* cited by examiner

*Primary Examiner* — Anastasia Midkiff
(74) *Attorney, Agent, or Firm* — Armstrong Teasdale LLP

(57) ABSTRACT

An X-ray lens is provided. The lens is located behind an X-ray tube and a collimator, the collimator located behind the X-ray tube, such that X-rays emitted from the X-ray tube pass through the collimator and then pass through the X-ray lens, wherein the X-ray lens is a monolithic capillary parallel lens configured to transform a cone emanant beam penetrating the collimator into parallel X-rays.

14 Claims, 3 Drawing Sheets

MONOLITHIC CAPILLARY PARALLEL X-RAY LENS

CROSS REFERENCE TO RELATED APPLICATIONS

This application claims the benefit of Chinese Patent Application No. 201010622822.5 filed Dec. 28, 2010, which is hereby incorporated by reference in its entirety.

BACKGROUND OF THE INVENTION

The present invention relates to the field of medical imaging, and in particular to an imaging technique for an X-ray medical image.

There are many factors impacting the imaging quality of an X-ray medical image, among which X-ray scattering is one of the most important factors. FIG. 1 shows scattered rays generated in an X-ray imaging system, wherein part of the scattered rays are generated from the X-rays emitted from the X-ray tube out of the focal spot (1). These scattered rays make up 25% of the rays originally emitted from the X-ray tube. If these rays cannot be effectively filtered, the patient will be radiated more than necessary, and the imaging quality will be impacted. In at least some current X-ray medical image devices, rays from the X-ray tube all penetrate the patient's body (3) after passing through the collimator (2) and being subjected to beam hardening. Before reaching the detector, the scattered rays among the X-rays are filtered by a grid. Before the X-rays penetrating the body (3), however, a significant amount of scattered rays of the X-rays are not filtered in any way. On the other hand, the dimension of the scattering angle also has a great influence on the X-ray imaging quality. FIG. 1 shows the X-ray scattering angle Φ (4). The optimum condition is achieved when Φ=90°. When Φ>90°, a larger Φ means that more rays from the X-ray source will scatter to deviate from the direction of the original rays. In at least some known current X-ray medical image devices, the scattering angle Φ is greater than 90° and is very large, even if a collimator (2) is used. Due to the above two phenomena, at least some current X-ray medical image devices will generate more scattered X-rays in application, which not only affects the image quality but also subjects the patient to more radiation than is necessary.

SUMMARY OF THE INVENTION

A method and device for improving X-ray imaging quality and reducing radiation on a patient is provided.

In one aspect, an X-ray lens is provided, which is placed behind the X-ray tube and the collimator behind the X-ray tube. X-rays, after emitting from the tube, pass through the collimator and then pass through the X-ray lens placed behind the collimator. The monolithic capillary parallel lens is placed behind the collimator to transform the cone emanant beam penetrating the collimator into parallel X-rays.

Inside the monolithic capillary parallel lens, there are several capillary cone pipelines.

The designed angles inside the capillary cone pipelines are greater than the angle of total reflection of the X-rays.

The material of the capillary cone glass pipelines is lead glass or lead ceramic.

A capillary parallel grid is placed behind the monolithic capillary parallel X-ray lens, and the gratings of the grid are aligned and parallel to the parallel emanating X-rays.

In another aspect, an X-ray system including an X-ray lens is provided.

The monolithic capillary parallel X-ray lens transforms the scattering angle Φ into 90°, preventing the scattering angle Φ from becoming too large and filtering the X-rays emitted from the X-ray tube out of the focal spot. The capillary parallel grid also helps filter scattered rays out of the focal spot before the rays reach the body. Therefore, the embodiments described herein can help to improve the image quality and reduce the radiation taken by the patient, and can also be applied to other medical image systems.

DETAILED DESCRIPTION OF THE INVENTION

Exemplary embodiments will be described in detail below, but the present invention is not limited thereto.

The exemplary embodiments described herein will be described in detail in conjunction with the drawings, but these embodiments are not intended to limit the present invention. The same components are denoted by the same reference numbers in different drawings.

Figure 1:
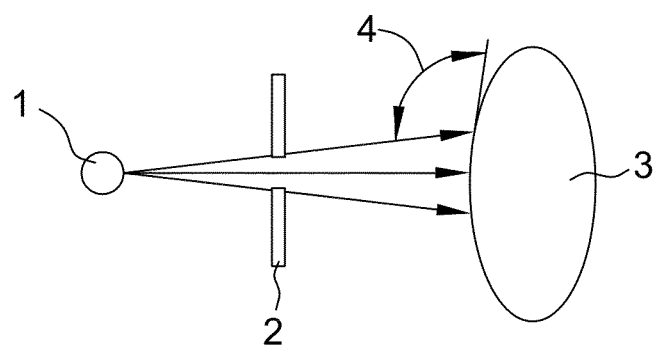
FIG. 1 shows scattered rays generated in an X-ray imaging system.
Figure 2:
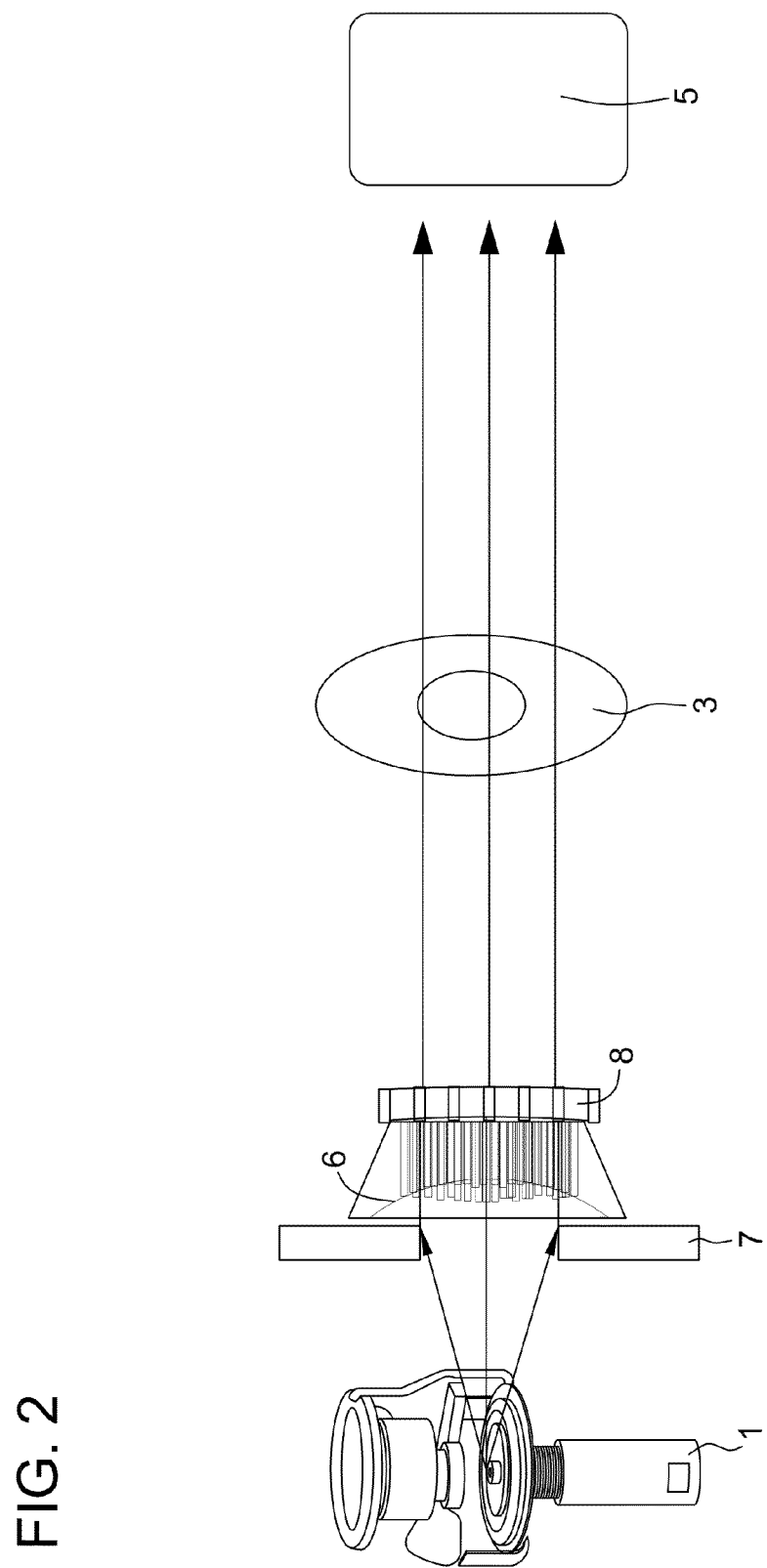
FIG. 2 shows an exemplary monolithic capillary parallel X-ray lens system.

FIG. 2 shows an exemplary monolithic capillary parallel X-ray lens system. The system uses a monolithic capillary parallel X-ray lens (6) to transform the cone scattered rays penetrating a collimator (7) into parallel X-rays, so that the X-rays are vertically incident on the patient's body (3). That is, the scattering angle Φ=90°. In addition, a capillary parallel grid (8) is added behind the monolithic capillary parallel X-ray lens (6), and gratings of the grid are aligned and parallel to the parallel emanant X-rays, thereby filtering around 60%-80% of the scattered X-rays emitted from the X-ray tube out of the focal spot (1). The capillary parallel grid (8) can be integrated at the end of the monolithic capillary parallel X-ray lens (6). The monolithic capillary parallel X-ray lens (6) transforms the scattering angle Φ into 90°, preventing the scattering angle Φ from becoming too large and filtering the X-rays emitted from the X-ray tube out of the focal spot. The capillary parallel grid (8) also helps filter scattered rays out of the focal spot before the X-rays reach the body.

Figure 3:
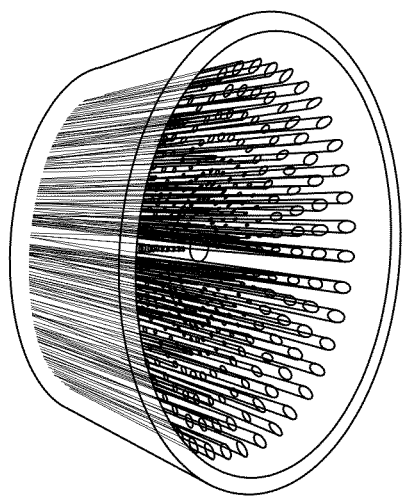
FIG. 3 shows a structural diagram of the monolithic capillary parallel X-ray lens shown in FIG. 2.

FIG. 3 shows a structural diagram of the monolithic capillary parallel X-ray lens shown in FIG. 2. Capillary cone pipelines may be used, the material of which may be lead glass or lead ceramic. When X-rays pass through, the capillary cone pipelines cause a series of reflection to the X-rays, and the designed angles θct inside the pipelines are greater than the angle of total reflection of the X-rays, which causes all the incident X-rays to pass through the pipelines and emanate parallelly after undergoing a series of total reflection when the incident angle of the X-rays is greater than θct. If the surfaces of the capillary cone pipelines are very smooth, then the transmissivity thereof will be high and the transformation into the parallel rays will be effective.

The monolithic capillary parallel X-ray lens can also be applied to other medical image diagnostic devices (e.g. CT devices) in addition to the X-ray medical image system and device.

The exemplary embodiments described herein are only for illustration. It shall be noted that those of ordinary in the art will be able to make many improvements, modifications and variations without departing from the spirit of the present invention. Such improvements, modifications and variations shall be considered as falling within the scope of the present application.

The invention claimed is:

1. An X-ray lens located behind an X-ray tube and a collimator such that X-rays emitted from the X-ray tube pass through the collimator and then pass through the X-ray lens, wherein the X-ray lens is a monolithic capillary parallel lens configured to transform a cone emanant beam penetrating the collimator into parallel X-rays, and wherein a capillary parallel grid is located behind the monolithic capillary parallel X-ray lens such that gratings of the capillary parallel grid are aligned and parallel to the parallel X-rays emanating from the monolithic capillary parallel X-ray lens.

2. The X-ray lens according to claim 1, wherein the monolithic capillary parallel lens comprises a plurality of capillary cone pipelines.

3. The X-ray lens according to claim 2, wherein designed angles inside the plurality of capillary cone pipelines are greater than an angle of total reflection of the X-rays.

4. The X-ray lens according to claim 3, wherein the plurality of capillary cone pipelines are made of one of lead glass and lead ceramic.

5. An X-ray system comprising an X-ray lens located behind an X-ray tube and a collimator such that X-rays emitted from the X-ray tube pass through the collimator and then pass through the X-ray lens, wherein the X-ray lens is a monolithic capillary parallel lens configured to transform a cone emanant beam penetrating the collimator into parallel X-rays, and wherein a capillary parallel grid is located behind the monolithic capillary parallel X-ray lens such that gratings of the capillary parallel grid are aligned and parallel to the parallel X-rays emanating from the monolithic capillary parallel X-ray lens.

6. The X-ray system according to claim 5, wherein the monolithic capillary parallel lens comprises a plurality of capillary cone pipelines.

7. The X-ray system according to claim 6, wherein designed angles inside the plurality of capillary cone pipelines are greater than an angle of total reflection of the X-rays.

8. The X-ray system according to claim 7, wherein the plurality of capillary cone pipelines are made of one of lead glass and lead ceramic.

9. A method of assembling an X-ray system, the method comprising:
   positioning a collimator behind an X-ray tube;
   positioning an X-ray lens behind the collimator such that X-rays emitted from the X-ray tube pass through the collimator and then pass through the X-ray lens, wherein the X-ray lens is a monolithic capillary parallel lens configured to transform a cone emanant beam penetrating the collimator into parallel X-rays; and
   positioning a capillary parallel grid behind the monolithic capillary parallel X-ray lens such that gratings of the capillary parallel grid are aligned and parallel to the parallel X-rays emanating from the monolithic capillary parallel X-ray lens.

10. The method according to claim 9, wherein positioning an X-ray lens comprises positioning an X-ray lens that includes a plurality of capillary cone pipelines.

11. The method according to claim 9, wherein positioning an X-ray lens comprises positioning an X-ray lens that includes a plurality of capillary cone pipelines made of one of lead glass and lead ceramic.

12. The method according to claim 9, wherein positioning an X-ray lens comprises positioning an X-ray lens that includes a plurality of capillary cone pipelines, wherein designed angles inside the plurality of capillary cone pipelines are greater than an angle of total reflection of the X-rays.

13. The X-ray lens according to claim 1, wherein the capillary parallel grid is integral with the monolithic capillary parallel X-ray lens.

14. The X-ray system according to claim 5, wherein the capillary parallel grid is integral with the monolithic capillary parallel X-ray lens.

* * * * *